United States Patent [19]

Tanimoto

[11] Patent Number: 4,586,822

[45] Date of Patent: May 6, 1986

[54] INSPECTING METHOD FOR MASK FOR PRODUCING SEMICONDUCTOR DEVICE

[75] Inventor: Akikazu Tanimoto, Yokohama, Japan

[73] Assignee: Nippon Kogaku K. K., Tokyo, Japan

[21] Appl. No.: 620,825

[22] Filed: Jun. 15, 1984

[30] Foreign Application Priority Data

Jun. 21, 1983 [JP] Japan ............................... 58-111534
Jun. 24, 1983 [JP] Japan ............................... 58-113857
Jun. 30, 1983 [JP] Japan ............................... 58-119421

[51] Int. Cl.$^4$ .......................................... G01N 21/00
[52] U.S. Cl. ................................. 356/394; 356/71; 356/389
[58] Field of Search ............... 356/71, 388, 389, 390, 356/394

[56] References Cited

U.S. PATENT DOCUMENTS

| | | | |
|---|---|---|---|
| 1,135,919 | 4/1915 | Pilkington | 356/71 |
| 2,470,877 | 5/1949 | Stuland | 356/394 |
| 4,385,838 | 3/1983 | Nakazawa et al. | 356/401 |
| 4,468,120 | 8/1984 | Tanimoto et al. | 356/237 |

*Primary Examiner*—R. A. Rosenberger
*Attorney, Agent, or Firm*—Shapiro and Shapiro

[57] ABSTRACT

A method for inspecting the presence of foreign particles on a mask comprising the steps of forming alignment marks on a wafer onto which the pattern is trially replicated, aligning projected images by means of the alignment marks to form overlapped images of the pattern of a mask to be inspected and the pattern of another mask in which the light and dark areas are inverted on a photosensitive material on the wafer, and inspecting the exposure status of the photosensitive material on the wafer after development to identify defects such as foreign particles attached to the mask to be inspected.

10 Claims, 30 Drawing Figures

INSPECTING METHOD FOR MASK FOR PRODUCING SEMICONDUCTOR DEVICE

BACKGROUND OF THE INVENTION

1. Field of the Invention

The present invention relates to a method for inspecting a photomask employed for replicating a circuit pattern onto a semiconductor wafer in the process for producing a semiconductor integrated circuit, and more particularly to a method for inspecting defects such as the presence of foreign particles affecting the replication of the pattern.

2. Description of the Prior Art

Recent development of finer and denser integrated circuit pattern has stimulated the widespread use of reduction projection exposure apparatus. In such apparatus, in which a pattern on a photomask called reticle is projected in a size reduced to 1/5 or 1/10 of the original size, foreign particles such as dusts on the reticle are replicated in reduced size in all the step-and-repeat exposures onto the wafer as long as they have a certain size and a certain optical density. In order to avoid such inconvenience, the resist image printed on the wafer has conventionally been observed, in trial manner, under microscope by human eyes to detect eventual replication of the foreign particles. This method however requires an extremely tiring work for the eye, for 2 to 3 hours at maximum per reticle, and may eventually overlook the foreign particles present. These drawbacks have only recently been resolved commercially by an apparatus which scans the reticle with a laser spot and detects the scattered light to identify the presence and dimension of the foreign particles, as disclosed in the Japanese Patent Application laid open No. 62543/1983, corresponding to the U.S. Pat. No. 4,468,120. Such apparatus is capable of automatic inspection within a short time, and detecting almost all foreign particles of a size large enough for replication. However the inspecting method employed in said apparatus is designed to satisfactorily distinguish foreign particles from the chromium layer, so that foreign particles lying flat on the chromium layer, if large enough in area, are sometimes mistaken as the chromium layer and not detected.

Also since this method does not directly inspect the replicated pattern, all the foreign particles of a size that may be replicated have to be detected. There has therefore been observed a tendency of detecting even small particles which are in fact not replicated and thus requesting excessive cleanness to the reticle.

Apart from the above-explained inspecting method, there is also considered a totally different inspecting method of overlaying and replicating a reticle to be inspected and another reticle, in which light and dark patterns are inverted, in succession onto a photosensitive material, and inspecting, after development thereof, the presence of spot patterns resulting from lack of exposure. This method has however suffered from insufficient precision in registration between a latent image formed by the first exposure through the reticle to be inspected and a projected image of the inverted pattern of the other reticle to be exposed next time, mainly due to a fluctuation in the positioning of the reticle in the exposure apparatus and to a drift in detecting the position of a stage supporting the wafer. In case the precision of registration of the first and second exposures is insufficient, there may be considered a method of increasing the exposure to increase the width of overlapped exposure of photoresist at the pattern edge, thus exposing the photoresist where the pattern edges are positionally aberrated to apparently cancel such aberration before the unexposed areas are inspected. In this method, however, the foreign particles present on the pattern edge become harder to be replicated and are often or totally overlooked at the inspection.

Besides, even if the positional registration is achieved with an optimum precision, such satisfactory registration cannot be obtained over the entire projection area if two reticles are exposed on different exposure apparatus because of the slightly different image distortion between the apparatus.

Finally, the detection of spot patterns formed on the photoresist layer has to be made by the eyes through a microscope with an objective lens of a high magnification and eventually through a television monitor, so that this method is still associated with a drawback of requiring visual observation in which the required labor is not significantly alleviated since this method only provides a simpler form in the objects of inspection. This method has not been applied to the practical use, since the above-mentioned drawback has become more serious with the recent development of finer circuit patterns.

SUMMARY OF THE INVENTION

A first object of the present invention is to provide a method for inspecting the presence of foreign particles on a mask by precisely registering a latent image formed by a first exposure with an image to be formed in a second exposure, thereby enabling detection of replicated images of even very small foreign particles.

According to the present invention, the above-mentioned object is achieved by a method which is featured by forming alignment marks on a wafer or the like onto which the pattern is trially replicated, aligning projected images by means of said alignment marks to form overlapped images of the pattern of a mask to be inspected and the pattern of another mask in which the light and dark areas are inverted on a photosensitive material on said wafer, and inspecting the exposure status of the photosensitive material on said wafer after development to identify defects such as foreign particles attached to said mark to be inspected.

A second object of the present invention is to provide a method for detecting the defects in the pattern such as replicated foreign particles with a high sensitivity with an apparently improved aligning precision even when a sufficient aligning precision cannot be obtained between the patterns of the mask to be inspected and of the inverted mask due to a distortion in the projection or an error in the magnification of the projection at the overlapped replication.

According to the present invention, the above-mentioned object is achieved by a method which is featured by forming, on a photosensitive surface, plural replication areas each formed by overlapped exposures of a pair of mutually inverted patterns, wherein said paired patterns are mutually shifted by a small distance in different directions respectively in said plural areas, and inspecting the exposure status of said plural replication areas after development of said photosensitive surface to detect the defects on the reticle to be inspected.

In an embodiment of the present invention, said inspection of the exposure status is conducted in a replication area where the overlapped exposures of the paired patterns are attained most precisely among said plural areas.

In another embodiment of the present invention, each of plural replication areas subjected to overlapped exposures is divided into plural partial areas, and said inspection of the exposure status is conducted in a partial area where the overlapped exposures are made most precisely among mutually corresponding partial areas of said plural replication areas.

A third object of the present invention is to provide a method for automatically detecting foreign particles on a mask with a high detection sensitivity.

According to the present invention, the above-mentioned object is achieved by a method which is featured by utilizing light scattering for example of laser beam in inspecting the photosensitive surface after development in the foregoing methods.

DESCRIPTION OF THE PREFERRED EMBODIMENTS

Figure 1:
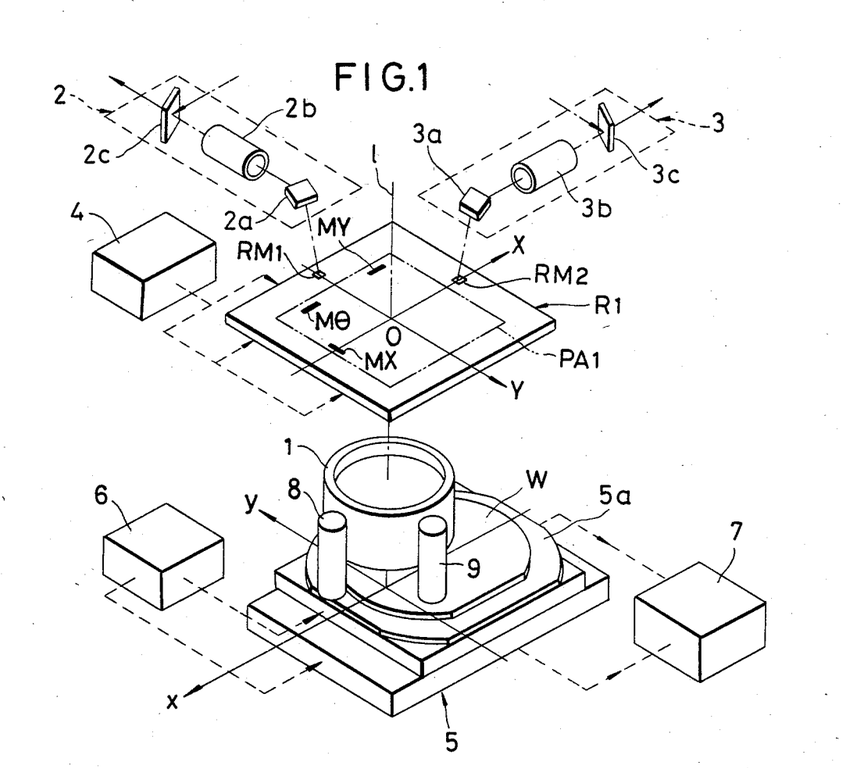
FIG. 1 is a schematic perspective view of a reduction projection exposure apparatus adapted for use in a replicating step in each embodiment of the present invention.

FIG. 1 shows a reduction projection exposure apparatus adapted for the method of the present invention, wherein a mark reticle R1, to be employed in a step for replicating marks in advance onto a wafer coated with a photoresist, is positioned above a projecting lens 1. The mark reticle R1 is provided, as shown in a plan view in FIG. 2, with marks RM1 and RM2 for reticle alignment in two positions.

Figure 2:
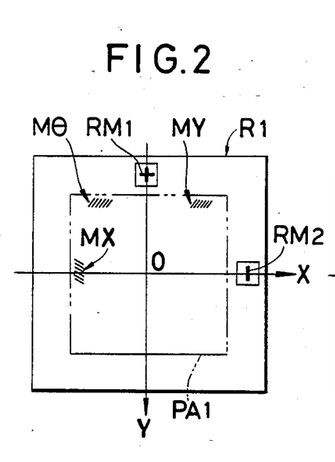
FIG. 2 is a plan view of a mark reticle.

In an orthogonal coordinate system XY having the original point at the center O of a replication area PA1 on the reticle R1, the mark RM1 is positioned on the Y-axis while the mark RM2 is positioned on the X-axis. The mark reticle R1 is also provided with three translucent marks MX, MY, M$\theta$ in the peripheral part of an opaque area PA1. The marks MY and M$\theta$ are positioned in two separate places in the system PA1 on a line parallel to the X-axis of said coordinate system, while the mark MY is positioned on a line parallel to the Y-axis. Each of said three marks MX, MY, M$\theta$ has a grating structure containing grating elements diagonal to the X and Y axes.

The mark RM1 of the mark reticle R1 is observed by a reticle alignment microscope 2 provided with a mirror 2a, an objective lens 2b, a half-mirror 2c etc. positioned at the side of an unrepresented light source (above), while the mark RM2 is observed by a reticle alignment microscope 3 composed of a mirror 3a, an objective lens 3b, a half-mirror 3c etc. The half-mirrors 2c, 3c are used for guiding the illuminating light to the objective lenses 2b, 3b. These two microscopes 2, 3 are respectively provided with references for aligning the observed images of the marks RM1, RM2. A driving unit 4 for two-dimensionally moving the reticle R1, including rotation thereof, so moves the reticle 1 that the displacements of the marks RM1, RM2 and the references of two microscopes 2, 3 decrease. Thus the reticle R1 is aligned to the exposure apparatus, whereby the optical axis l of the projecting lens 1 is so positioned to pass through the center O of the reticle R1.

Immediately under the projecting lens 1 a wafer W is positioned so that the pattern of the reticle is projected onto said wafer W. Said wafer W is placed on a two-dimensionally movable stage 5 and is therefore rendered movable in x- and y-directions of an orthogonal coordinate system xy by means of a driving unit 6. The stage 5 is provided with a wafer holder 5a capable of fixing the wafer W by suction and rotatable in the x-y plane with respect to the stage 5. A coordinate position detector 7 measures the two-dimensional position of the stage 5 with respect to a determined original point, for example the optical axis l, for example by measuring the amounts of displacement of the stage 5 in the x- and y-directions with a laser interferometer. Around the projecting lens 1 there are provided two wafer alignment microscopes 8, 9. The microscope 8 is so positioned that the optical axis thereof is parallel to the optical axis l of the projecting lens 1, and that said optical axis, or the center of observation, crosses the x-axis of the coordinate system xy of which original point is on the optical axis l.

On the other hand, the microscope 9 is so positioned that the optical axis thereof is parallel to the optical axis l of the projecting lens 1 and that said optical axis or the center of observation crosses the y-axis of the coordinate system xy. The microscope 8 is used for detecting the wafer position in the x-direction by observing the mark on said wafer, while the microscope 9 is used for detecting the wafer position in the y-direction by observing the mark on said wafer.

The reticle alignment microscopes 2, 3 and the wafer alignment microscopes 8, 9 have, in addition to the visual observation, a function of photoelectric microscope by causing relative vibration between the observed image of the mark and a slit and photoelectrically detecting the displacement of the image of the mark with respect to the center of said vibration, which is the aforementioned reference or the center of observation.

Particularly the microscopes 8, 9 are preferably provided with a function of so-called laser scanning microscope of causing a small vibration of a laser beam spot on the wafer and photoelectrically detecting the light scattered or diffracted by the mark on the wafer to identify the displacement of the mark with respect to the center of vibration of the laser beam spot.

Figure 3:
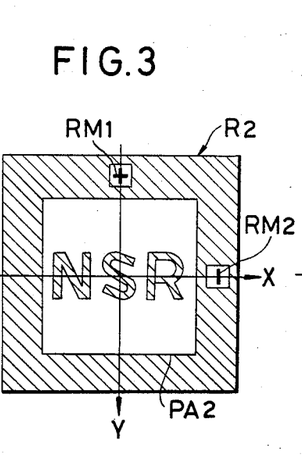
FIG. 3 is a plan view of a reticle to be inspected, having a positive pattern.

FIG. 3 is a plan view of an example of the reticle R2 to be inspected, having a true pattern to be replicated onto the wafer W. The dimension of a replication area PA2 of the reticle R2 to be inspected is same as that of the replication area PA1 of the mark reticle R1, and said reticle R2 is provided with marks RM1, RM2 in the same manner and in the same positions as the marks RM1, RM2 of the reticle R1. In FIG. 3, the hatched area is composed of an evaporated opaque chromium layer, while the translucent glass plate remains in the other area. The pattern in the replication area PA2 will hereinafter be called positive pattern for the ease of explanation.

Figure 4:
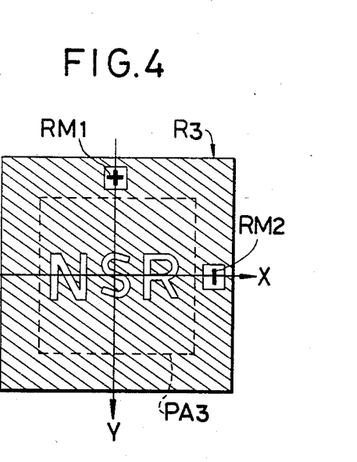
FIG. 4 is a plan view of an inverted reticle having a negative pattern.

On the other hand, FIG. 4 is a plan view of an inverted reticle R3 prepared for executing the method of the present invention. The inverted reticle R3 is provided with marks RM1, RM2 in a similar manner and in the same positions as in the reticles R1 and R2. The dimension of a replication area PA3 is same as that of the area PA2 in the reticle R2. The pattern in the area PA3 corresponds to the positive pattern in the area PA2 and is formed as a negative pattern in which the translucent and opaque areas are inverted.

The reticle R2 to be inspected and the inverted reticle R3 are prepared by a knwon process of exposing a photoresist layer provided on a chromium-evaporated transparent substrate to electron beam irradiation. For the purpose of preparing the reticle R2, design data for forming the true pattern are given to an electron beam irradiating apparatus. On the other hand, at the preparation of the reticle R3, inverted data are prepared by inverting said design data and are given to the electron beam irradiating apparatus.

In the present invention, not only a reticle or a photomask is regarded as a pattern-bearing transparent substrate, but also such substrate provided with a dust-preventive thin layer is called reticle or photomask.

FIGS. 5A to 5E show replication steps in a first embodiment of the inspecting method of the present invention.

Figure 5A:
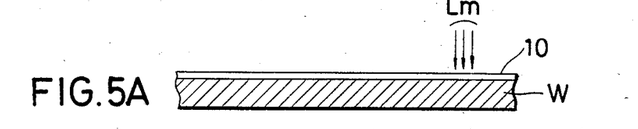
FIGS. 5A to 5E are schematic views showing replicating steps in a first embodiment of the present invention.

At first a positive photosensitive material is coated on the wafer W to form a uniform positive resist layer 10, which is subsequently baked. Said wafer is placed on the wafer holder 5a of the exposure apparatus as shown in FIG. 1. In this state the wafer is positioned, by means of a peripheral notch, called orientation flat, to the wafer holder 5a. In the present embodiment the direction of said orientation flat is selected parallel to the x-axis moving direction of the movable stage 5.

On the other hand, the mark reticle R1 shown in FIG. 2 is positioned to the exposure apparatus as shown in FIG. 1. Then there is repeated a step of moving the stage 5 in the x- and y-directions by a determined pitch through the driving unit 6 in response to the measurement of the detector 7 and illuminating the area PA1 of the reticle R1 for a determined period, thus guiding light beams Lm from the marks MX, MY, M$\theta$ of the reticle R1 to the positive resist layer 10 on the wafer, thereby forming reduced latent images of the marks MX, MY, M$\theta$ in said layer.

Figure 5B:
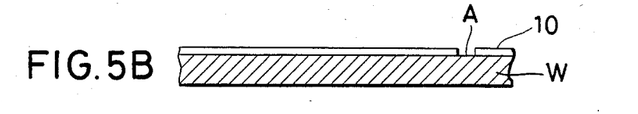
Figure 6:
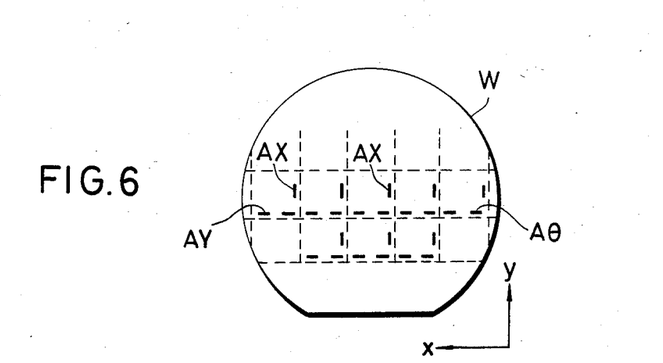
FIG. 6 is a plan view showing the arrangement of marks on a wafer.

Then the wafer is removed from the wafer holder 5a and the resist layer 10 is developed, whereby the resist corresponding to the latent images of the marks MX, MY, M$\theta$ is removed to obtain recessed marks A corresponding to the marks MX, MY, M$\theta$ as shown in FIG. 5B. On the wafer, as shown in FIG. 6, said marks A are formed in the replication areas as the marks AX, AY, A$\theta$ respectively corresponding to the marks MX, MY, M$\theta$. Naturally said marks AX, AY, A$\theta$ are provided with diagonal lattice structure.

Then the mark reticle R1 is removed from the exposure apparatus, and the inverted reticle R3 shown in FIG. 4 is positioned to the exposure apparatus by means of the marks RM1, RM2.

On the other hand, the wafer shown in FIG. 6 is again placed on the wafer holder 5a and is positioned thereto by means of the orientation flat. The photoresist material constituting the positive resist layer should preferably retain the photosensitive property after the image development. If the resist material loses the photosensitive property by the image development, a resist layer must be formed again on the wafer shown in FIG. 6.

When the wafer is fixed on the wafer holder 5a by vacuum suction, the position of said wafer to the exposure apparatus is usually aberrated slightly from the wafer position at the replication of the reticle R1.

Therefore, the wafer W is positioned again to the exposure apparatus through the use of the microscopes 8, 9. The positioning procedure will be briefly explained herein as it was detailedly disclosed in the U.S. Pat. No. 4,385,838.

At first, among plural marks AY, A$\theta$ formed on a particular line in the x-direction parallel to the orientation flat, a pair of marks AY, A$\theta$ positioned closest to the periphery of the wafer is used for detecting the rotational error and the position in y-direction of the wafer. For this purpose the stage 5 is moved in such a manner that the mark AY at the left-hand end of the wafer coincides with the center of observation in the y-direction of the microscope 9. Then the stage 5 is moved in the x-direction, and the mark A$\theta$ at the right-hand end of the wafer is observed by the microscope 9. Then, from this position, the stage 5 is moved in the y-direction until the mark A$\theta$ coincides with the center of observation in the y-direction of the microscope 9.

The amounts of stage movements in the x- and y-directions in the above-mentioned steps are detected by the detector 7 to determined the rotational error of the wafer to the coordinate system xy. This rotational error can be corrected within a certain limit by the rotation of the wafer holder 5a, but a more precise correction is achieved, as disclosed in the aforementioned U.S. Pat. No. 4,385,838, by forming a coordinate system which is rotated from the coordinate system xy by a small amount corresponding to the slight rotational error of the wafer and positioning the stage according to thus formed coordinate system at the step movement of the stage 5 for exposure.

After the amount of rotation of the wafer to the coordinate system xy is determined in this manner, the y-coordinate value is determined when the mark AY at the left-hand end of the wafer coincides with the center of observation in the y-direction of the microscope 9, and then the y-coordinate value is determined when a particular mark AX on the wafer coincides with the center of observation in the x-direction of the microscope 8. In this manner the positional relationship of the wafer in the x- and y-directions with respect to the optical axis 1 of the projecting lens 1.

Figure 5C:
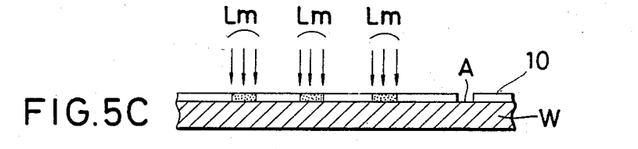

Then there is conducted repeated a step of stepwise moving the stage 5 with a same pitch as in the exposures of the mark reticle R1 by means of the driving unit 6 and the detector 7 following the already replicated marks AX, AY, A$\theta$, and illuminating the replication area PA3 of the inverted reticle R3, thereby replicating the negative pattern in succession onto the wafer. In this step the wafer is so positioned that the marks AX, AY, A$\theta$ are present around the projected image of the area PA3, in order to avoid the exposure of said marks AX, AY, A$\theta$. FIG. 5C shows the step of negative pattern exposure, wherein a light beam Lm through the transparent area of the reticle R3 is guided to the resist layer 10 to form a reduced latent image of the negative pattern in said resist layer 10. In said stepwise exposures of the negative pattern. One of plural replication areas on the wafer having the marks AX, AY, A$\theta$ is excluded from the exposure of the negative pattern.

Then the positive pattern of the reticle R2 to be inspected is replicated onto the latent image formed in the resist layer 10 of said wafer.

For this purpose the reticle R3 is removed from the exposure apparatus, and the reticle R2 is set and positioned on the exposure apparatus by means of the marks RM1, RM2. In this state, therefore, the reticle R2 is aligned with the wafer on the stage 5 indirectly through the exposure apparatus, taking the marks AX, AY, A$\theta$ as references.

Figure 5D:
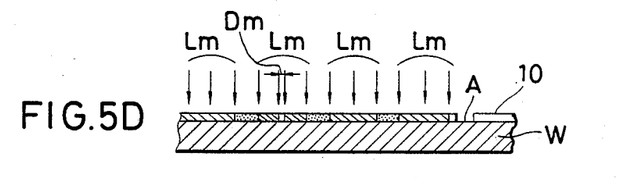

Then there is repeated a step of moving the stage 5 to a position same as that for the stepwise exposure of the negative pattern in such a manner that the projected image of the positive pattern of the reticle R2 to be inspected is superposed on the previously replicated latent image of the negative pattern of the inverted reticle R3, and illuminating the area PA2 of the reticle R2. Also in this case the marks AX, AY, A$\theta$ are excluded from the exposure. FIG. 5D shows the state of this exposure. If the transparent area of the reticle R2 is free from foreign particles, a light beam Lm irradiates the entire resist layer 10 except the area irradiated by the light Lm in FIG. 5C, thereby forming a reduced latent image of the positive pattern. However, a foreign particle, if present, intercepts the illuminating light to form a dark area Dm corresponding to the foreign particle in the light beam Lm as shown in FIG. 5D. The resist layer 10 is not exposed in said dark area Dm. Thus the resist layer 10 forms an unexposed area due only to the foreign particles adhered to the reticle R2. In this manner the negative and positive patterns are replicated, in mutually superposed manner, onto the resist layer 10. The area of the wafer not exposed to the negative pattern is exposed only to the positive pattern of the reticle R2.

Figure 5E:
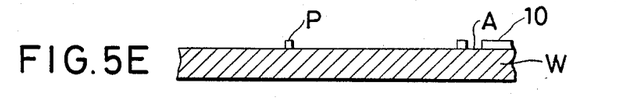

Subsequently the wafer W is removed from the exposure apparatus and is subjected to the development of the resist layer 10, whereby the areas exposed to the positive and negative patterns are removed the unexposed area resulting from the adhered foreign particle subsists on the wafer surface as a remaining resist P as shown in FIG. 5E.

As explained in the foregoing, minute foreign particles present in the transparent area of the reticle to be inspected are clearly marked on the wafer as indicia, which can be detected and of which positions can be determined by a wafer inspecting apparatus to be explained later. In the above-described method the foreign particles present in the transparent area of the inverted reticle are similarly marked on the wafer, but the positions of the indicia on the wafer allow to identify whether the foreign particles are present on the reticle to be inspected or on the inverted reticle. However, a defect not present in the transparent area of either reticle, for example a pinhole present in the opaque area of the reticle or a partial lack at the edge or corner of the chromium pattern does not form a remaining resist on the wafer. Consequently the defect in the opaque area cannot be detected by the superposed replication of the reticles R2, R3 shown in FIGS. 3 and 4.

Figure 7A:
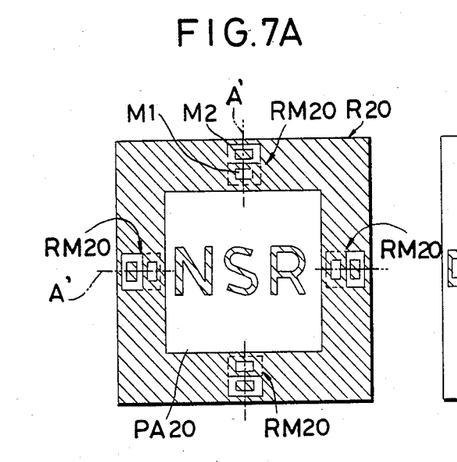
FIG. 7A is a plan view of a reticle to be inspected, having a positive pattern.
Figure 7B:
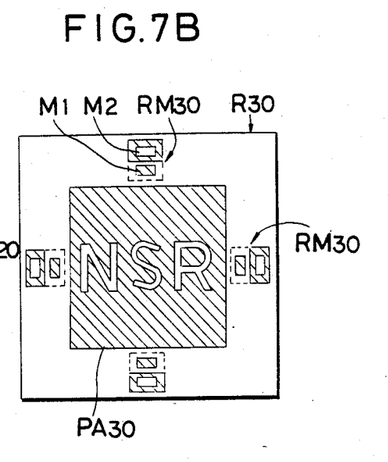
FIG. 7B is a plan view of an inverted reticle having a negative pattern.
Figure 8A:
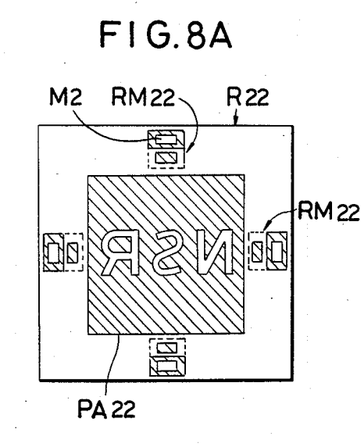
FIG. 8A is a plan view of the reticle to be inspected, having a negative pattern formed by the replication of the pattern of the reticle shown in FIG. 7A.
Figure 8B:
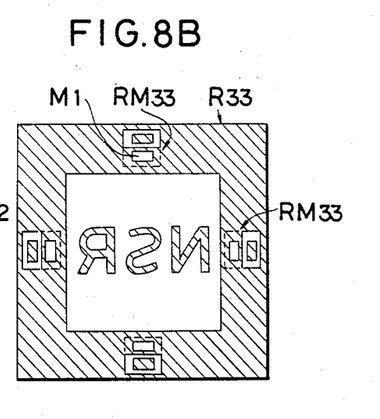
FIG. 8B is a plan view of the inverted reticle having a positive pattern formed by the replication of the pattern of the reticle shown in FIG. 7B.

FIGS. 7 and 8 show another embodiment enabling the detection of foreign particles present in the transparent area of reticles and of defects present in the opaque area.

A reticle R20 to be inspected, shown in FIG. 7A, is provided with four alignment marks RM20 around a replication area PA20. Each alignment mark is composed of a pair of marks, namely a transparent mark M1 surrounded by an opaque area and an opaque mark M2 surrounded by a transparent area. The pattern and the marks of said reticle R20 can be prepared, as in the case of FIG. 3, by electron beam exposure according to design data.

An inverted reticle R30 shown in FIG. 7B is provided with alignment marks RM30 and a pattern in a replication area PA30, both inverted from the reticle shown in FIG. 7B, and can be prepared for example by electron beam exposure according to inverted design data.

The pattern of said paired reticles R20, R30 are replicated on a wafer W in superposed manner through steps similar to those shown in FIGS. 5A to 5E to detect the foreign particles present in the transparent area. The marks RM20, RM30 are used for alignment between the reticles and the wafer. When the reticle R20 is set on the exposure apparatus shown in FIG. 1, the marks M1 are used to enable observation of images A' (represented by chain lines in FIG. 7A) of reference marks of the wafer projected on the reticle, while the other marks M2 are used when the reticle 30 is set on said apparatus.

A reticle R22 shown in FIG. 8A is provided with a negative pattern laterally inverted from the pattern of the reticle R22 to be inspected shown in FIG. 7A. The negative pattern of the reticle R22 is prepared by replicating, either by contact or proximity printing, the entire pattern of the reticle R20 onto a negative photoresist coated on a substrate. In this step the pattern bearing face of the reticle R20 is so positioned as to face the substrate to be exposed and the illumination is made from the rear face of said reticle R20, so that a laterally inverted negative pattern is formed in the replication area PA22 of the reticle R22. Different from the negative pattern of the inverted reticle R30 shown in FIG. 7B, the negative pattern prepared as explained above also contains the defects of the reticle R20 to be inspected.

A reticle R33 shown in FIG. 8B has a positive pattern laterally inverted from the pattern of the inverted reticle R30 shown in FIG. 7B. The positive pattern of the reticle R33 is prepared from the inverted reticle R30 in a similar manner as the reticle R22, and therefore contains the defects present on the inverted reticle R30.

Two reticles R22, R33 thus prepared are aligned to the wafer by means of the marks M2 of the marks RM22 and the marks M1 of the marks RM33 and are replicated in succession on the wafer to form, on said wafer, indicia of the foreign particles present in the transparent area of the reticles R22, R33 corresponding to the defects in the opaque area of the reticles R20, R30.

Consequently a complete inspection of the reticle to be inspected is achieved by detection and positional determination of the remaining resists on the first wafer prepared by superposed replication of the reticles R20, R30 and on the second wafer prepared by superposed replication of the reticles R22, R33.

In the following there will be given an explanation on an embodiment of the wafer inspecting apparatus. The following description will deal with the inspection of the first wafer only, since the first and second wafers can be inspected in the same manner.

Figure 9:
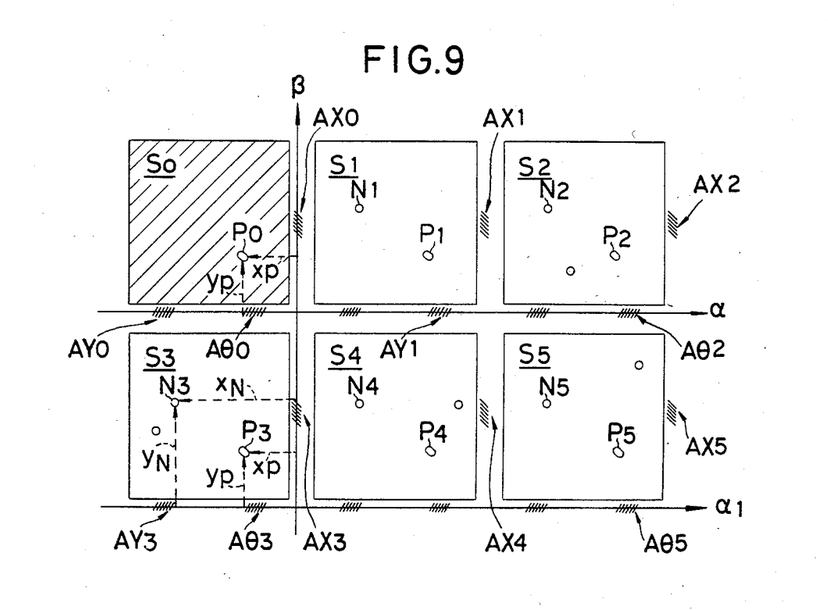
FIG. 9 is a plan view showing a group of replicated patterns.

In a first embodiment of wafer inspection, a group of patterns as shown in FIG. 9 is formed on the wafer W after image development. In FIG. 9 there are only shown representative six replication areas S0-S5 arranged in matrix form. It is assumed that the positive pattern of the reticle R2 to be inspected is alone replicated in the area S0, while the positive and negative patterns are superposedly replicated in other areas S1-S5. It is further assumed that the six areas S0-S5 are positioned at a determined pitch in relation to an orthogonal coordinate system $\alpha\beta$ defined on the wafer.

At the wafer inspection, one compares said areas S1-S5 and determines whether the remaining resists P1-P5 or N1-N5 exist in the corresponding positions of said areas. Remaining resists which do not appear in the corresponding positions but in random positions can be considered to have resulted from dusts present on the photoresist of the wafer prior to the exposure, or from deposition of fine particles of the photoresist at the image development step. In such case it is therefore possible to conclude that the foreign particle is not present at the corresponding position on the reticle R2.

After confirming the presence of remaining resists P1-P5, N1-N5 in the corresponding positions of the areas S1-S5, one determines whether similar remaining resists exist in the corresponding positions in the area S0. In the illustrated example, a remaining resist P0 exists, in the positive pattern of the area S0, in a position corresponding to that of the remaining resists P1-P5, whereas no resist is found in a position corresponding to that of the remaining resists N1-N5. Consequently the remaining resistors P0-P5 are identified to have resulted from a foreign particle adhered to the transparent area of the reticle R2, while the remaining resists N1-N5 are identified to have resulted from a foreign particle adhered to the transparent area of the inverted reticle R3. It is therefore rendered possible to conclude that a foreign particle, affecting the production yield in the lithographic process, is present in a position of the reticle R2 corresponding to the position of the remaining resist P0 in the area S0.

Figure 10:
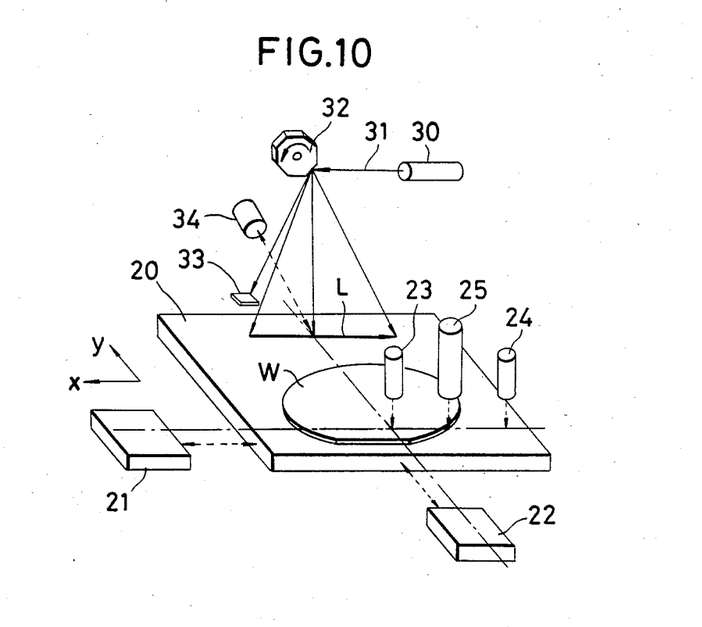
FIG. 10 is a schematic perspective view of a laser scanning inspecting apparatus adapted for use in an inspecting step in the embodiments of the present invention.

FIG. 10 shows an embodiment of the wafer inspecting apparatus suitable for such inspection.

The wafer W after image development is placed on a two-dimensionally movable table 20, which can be displaced in mutually orthogonal directions x, y. As in the exposure apparatus shown in FIG. 1, the table 20 is provided with a wafer holder which is rotatable to said table 20 and is driven by an unrepresented driving unit. The wafer is in fact placed on said wafer holder and is fixed by suction. The positions of said table 20 in the x- and y-directions are detected as coordinate values by position detectors 21, 22 utilizing for example laser interferometers or optical linear encoders. On the crossing point of the mutually orthogoanl measuring lines of the position detectors 21, 22, there is provided an XY-microscope 23 in such a manner that the optical axis or the center or observation coincides with said crossing point. Said XY-microscope 23 is provided with a function of photoelectric or laser scanning microscope for detecting the marks AX, AY (or $A\theta$) on the wafer, and is utilized to achieve wafer alignment in the x- and y-directions.

There is further provided a $\theta$-microscope 24 for detecting the mark $A\theta$ (or AY) on the wafer to achieve wafer alignment in the y-direction, and the optical axis or the center of observation is positioned on the measuring line in the x-direction of the position detector 21. The distance between the optical axes or the centers of observation of the XY-microscope 23 and $\theta$-microscope 24 is so selected as to enable simultaneous observation of two distant marks, for example the marks AY and $A\theta$, on the wafer.

Furthermore there is provided a microscope 25 for visually observing the wafer surface and confirming the resists remaining thereon.

On the other hand there is provided a laser scanning device for detecting the remaining resists. A laser beam 31 emitted from laser uhit 30 enters a polygonal mirror 32 rotated anticlockwise at a determined speed, and is focused into a spot by means of an unrepresented focusing lens, thus performing a linear scanning motion at a constant speed in the x-direction along a trajectory L. The scanning trajectory L is placed at a predetermined position to the microscopes 23, 24, 25. There are also provided a photosensor 33 for timing detection at the start of the scanning trajectory L, and a photoelectric detector 34 for detecting the light scattered from the edges of minute surface irregularities such as remaining resists illuminated by the laser beam spot when the table 20 is so moved that the scanning trajectory L crosses the wafer. Said photoelectric detector 34 is provided with a condenser lens of a determined steric entrance angle for receiving the light scattered from any part of the scanning trajectory L. The optical axis of the detector 34 diagonally looks at the center of the scanning trajectory L. The laser beam 31 enters the wafer surface preferably in substantially perpendicular direction, in order to precisely determine the incident position of the laser beam.

The detection of the remaining resists on the wafer is achieved by raster scanning the wafer with the laser beam spot, by displacing the table 20 in the y-direction while causing the laser beam spot to scan in the x-direction.

The operation of remaining resist detection is achieved by the above-described wafer inspecting apparatus in the following manner.

At first a wafer W as shown in FIG. 6 is positioned, by means of the orientation flat thereof, on the wafer holder on the table 20. The orientation flat is positioned to be parallel to the x-direction as shown in FIG. 10.

Figure 11:
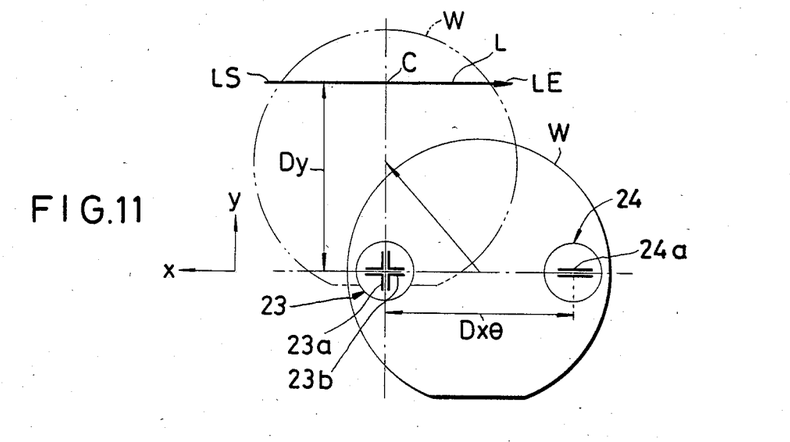
FIG. 11 is a schematic view showing the principle of wafer positioning in the laser scanning inspecting apparatus.

Then the table 20 is so moved that the wafer is positioned under the microscopes 23, 24 as shown in FIG. 11, and one of the marks AY on the wafer is observed by the XY-microscope 23 while one of the marks $A\theta$ on the wafer is observed by the $\theta$-microscope.

For the ease of following description, it is assumed that said mark AY is the mark $AY_3$ in the area S3 in FIG. 9, and said mark $A\theta$ is the mark $A\theta_5$ in the area S5. Consequently the distance between the marks $AY_3$ and $A\theta_5$ is selected equal to the distance $Dx\theta$ between the microscopes 23 and 24. In FIG. 9, a coordinate axis passing through the marks $AY_3$ and $A\theta_5$ will be called $\alpha_1$.

Then the table 20 is so displaced that the mark $AY_3$ coincides with a reference 23b in the y-direction of the XY-microscope 23, and the wafer holder is so rotated that the mark $A\theta_5$ coincides with a reference 24a in the y-direction of the $\theta$-microscope 24. In this manner the wafer is aligned in rotational direction.

In this state, in a counter (hereinafter called $\beta$-counter) of the position detector 22, there is preset a value corresponding to a distance Dy from the reference 23b of the XY-microscope 23 to the scanning trajectory L of the laser beam spot.

Subsequently the table 20 is so displaced in the x-direction that one of the marks AX on the wafer, i.e. the mark $AX_3$ in the area S3 in the illustrated case, coincides with the reference 23a in the x-direction of the XY-microscope 23. Then a counter (hereinafter called $\alpha$-counter) of the position detector 21 is preset for example to zero.

The above-described procedure allows the wafer to be positioned with respect to the scanning trajectory L of the laser beam spot. More specifically, the scanning trajectory L coincides with the coordinate axis $\alpha_1$ of the coordinate system $\alpha_1\beta$ on the wafer when the $\beta$-counter is brought to zero by the displacement of the table 20, and the center C of the scanning trajectory L coincides with the coordinate axis $\beta$ when the $\alpha$-counter is brought to zero. Consequently the coordinate values represented by the $\alpha$- and $\beta$-counters indicate the position of the scanning trajectory L on the coordinate system $\alpha_1\beta$.

Then the wafer is positioned under the scanning trajectory L of the laser beam spot, and the table 20 is moved at a constant speed in the y-direction, or in the $\beta$-direction on the wafer.

In the following there will be explained a case in which the scanning trajectory L is positioned on the coordinate axis $\alpha_1$ and three areas S3, S4, S5 shown in FIG. 9 are scanned by the laser beam spot.

Figure 12A:
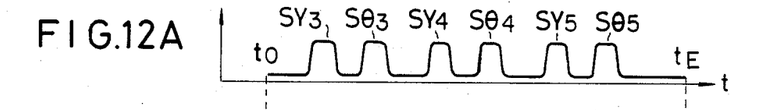
FIGS. 12A to 12C are wave form charts showing photoelectric output signals corresponding to laser beam scanning.

In response to the scanning of the laser beam spot along the coordinate axis $\alpha_1$, the photoelectric detector 34 releases time-sequential photoelectric signals as shown in FIG. 12A. A time $t_0$ indicates when the laser beam spot is positioned at a start point Ls of the scanning trajectory L, and a time $t_E$ indicates when the laser beam spot is positioned at an end point $L_E$ of said trajectory L.

Said photoelectric signals assume peak values $SY_3$, $S\theta_3$, ..., $S\theta_5$ respectively corresponding to the scattered lights from the marks $AY_3$, $A\theta_3$, $AY_4$, $A\theta_4$, $AY_5$ and $A\theta_5$.

By reading the value of the $\beta$-counter of the position detector 22, it is easily presumably that the photoelectric signals shown in FIG. 12A are not caused by the remaining resists but by the scattered light from the marks AY, $A\theta$.

Figure 12B:
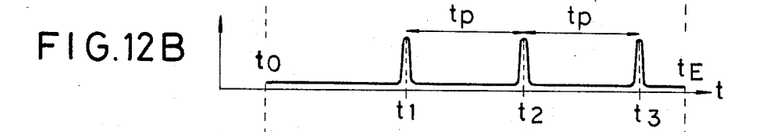

When the scanning trajectory L crosses the marks $AX_3$, $AX_4$ and $AX_5$ by the continued displacement of the table 20 in the y-direction, the photoelectric detector 34 releases periodic photoelectric pulse signals of an interval $t_p$, in the order of $t_1$, $t_2$, $t_3$, ... as shown in FIG. 12B, respectively corresponding to the marks $AX_3$–$AX_5$. Thus, the distance from the start point $L_s$ of the trajectory L to the mark $AX_3$ can be determined by a counter which starts counting of reference clock pulses in response to the output signal from the photosensor 33 at a time $t_0$ of the irradiation of the laser beam spot and terminates said counting in response to the first pulse at a time $t_1$ of the photoelectric signals.

On the other hand the wafer is positioned at a determined relation to the trajectory L, and the dimensions of the areas S0–S5 and the positions of the marks AX, AY, $A\theta$ are already known at designing or at exposures. Thus the distance from the start point $L_s$ to the mark $AX_3$ can be determined from the contents of the position detectors 21, 22.

Consequently, if the pulse position at a time $t_1$ determined from the reference clock pulses substantially coincides with the position of the mark $AX_3$ determined from the coordinate values of the position detectors 21, 22, it is possible to identify that, among the pulses in said photoelectric signals, pulses appearing at the interval $t_p$ starting from the time $t_1$ are not generated by the remaining resists but by the scattered light from the marks $AX_3$, $AX_4$ and $AX_5$.

Figure 12C:
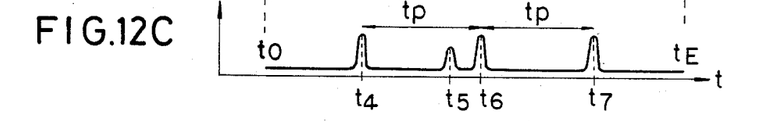

In case the scanning trajectory L of the laser beam spot passes through the remaining resists P3, P4, P5 in the mutually corresponding positions of the areas S3, S4, S5, the photoelectric detector 34 releases photoelectric pulse signals at times t4, t5, t6, t7 as shown in FIG. 12C. The pulses at t4, t6 and t7 are generated by the scattered light from the remaining regists P3, P4 and P6, while the pulse at t5 is generated by the scattered light from randomly remaining resist particles.

Figure 13:
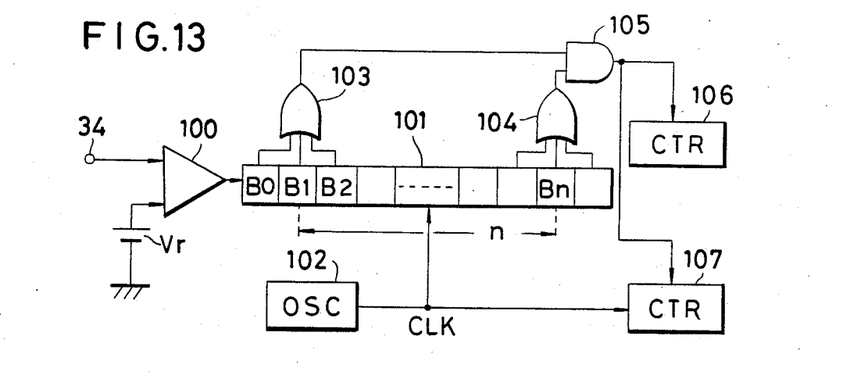
FIG. 13 is a block diagram showing an example of a circuit for processing the photoelectric signals in the laser scanning inspecting apparatus.

Such photoelectric signals, composed of three pulses at an interval $t_p$, indicate the presence of mutually corresponding resists remaining in the areas S3, S4 and S5, and the position of such remain-resists P3, P4, P5 can be determined at high speed for example with a digital correlator as shown in FIG. 13. The photoelectric signals from the photoelectric detector 34 are binary encoded by comparison with a determined slice voltage Vr in a comparator 100. Consequently the pulses in the photoelectric signals are encoded as "1" and the remaining part is encoded as "0". The binary encoded output signals from the comparator 100 are supplied, bit by bit, into the left-end bit of a shift register 101, which has at least n bits and shifts the contents to the right bit by bit in response to reference clock pulses CLK released from an oscillator 102 from a time $t_0$ to a time $t_E$.

The shift of n bits of the shift register 101 is achieved by n clock pulses CLK which are released from the oscillator 102 in a period equal to the interval $t_p$. An OR gate 103 receives binary signals from the three bits at the entrance side of the register 101, and supplies a signal "1" to an AND gate 105 if any of said three bits is at the state "1". An OR gate 104 receives binary signals from three bits at the exit side, distant by n bits from the above-mentioned three bits, of the register 101, and supplies a signal "1" to the AND gate 105 if any of said three bits is in the state "1". Thus, the AND gate 105 releases a signal "1" only when the OR gates 103, 104, both releases the signals "1".

A counter 106 counts the number of the signals "1" released from the AND gate 105 between $t_0$ and $t_E$. A counter 107 counts the clock pulses CLK from $t_0$ and terminates the counting when the AND gate 105 releases the signal "1".

In such circuit structure, when the photoelectric signals as shown in FIG. 12C are generated from time $t_0$, signals "0" are stored and shifted from the first bit $B_0$ at the entrance side of the shift register 101 until $t_4$, when a signal "1" is stored in response to the photoelectric pulse signal. The signal shifting proceeds further, and signals "1" are stored at $t_5$ and $t_6$. In this state a bit $B_n$ stores a signal "1" in response to the pulse at $t_4$, while a bit $B_1$ or $B_0$ stores a signal "1" in response to the pulse at $t_6$, whereby the AND gate releases a signal "1". Consequently the counter 106 stores a count "1" and the counter 107 counts the clock pulses CLK from $t_0$ to $t_6$.

With a further progress of the signal shifting along the proceeding of scanning with the laser beam spot, a signal "1" corresponding to the pulse at $t_6$ is stored in the bit $B_n$ while a signal "1" corresponding to the pulse at $t_7$ is stored in the bit $B_1$, so that the AND gate releases a signal "1". Thus the counter 106 stores a count "2".

Thus, after the completion of a scanning operation of the laser beam spot, the presence of corresponding remaining resists P3, P4, P5 on the scanning trajectory L is confirmed if the content of the counter 106 is less, by one, than the number of replication areas to be investigated. The position $y_p$ of the remaining resist P3 in the y-direction on the coordinate system $\alpha_1\beta$ can be determined by latching the content of the $\beta$-counter of the position detector 22 when the content of the counter 106 becomes equal to "2". Also the distance in the x-direction from the start point Ls of the scanning trajectory L to the remaining resist P3 is obtained by subtracting n (corresponding to the interval $t_p$) from the content of the counter 107. Furthermore the position $x_p$ of the remaining resist P3 in the x-direction on the coordinate system $\alpha_1\beta$ can be determined from the content of the counter 107, since the distance from the start point Ls to the mark AX3 is known as already explained in relation to FIG. 12B.

As explained in the foregoing, at least two replication areas prepared by superposing a positive pattern and a negative pattern on a wafer are examined to determine the coordinate values $(x_p, y_p)$ and $(x_N, y_N)$ of the remaining resists P, N in the mutually corresponding positions. Then the table 20 is moved according to said coordinate values, and a confirmation is made through the microscope 25 whether the remaining resist $P_0$ or $N_0$ exist at the same coordinate value $(x_P, y_P)$ or $(x_N, y_N)$ in the coordinate system $\alpha\beta$ in the area S0 of the wafer. In this case the remaining resist $P_0$ alone is found.

Consequently, although the final confirmation still has to be made by the operator, the presence of foreign particles on the reticle R2 can be detected with a much less effort than in the conventional method in which the entire surface of the area S0 has to be inspected from the beginning. Also at the observation of the area S0 with the microscope 25, the table 20 is automatically positioned to the preselected coordinate $(x_P, y_P)$, $(x_N, y_N)$, so that the operator need only to watch a television image of the wafer surface obtained through the microscope 25.

In the foregoing embodiments, the range of the raster scanning with the laser beam spot is confined to the areas S3, S4 and S5 arranged in the x- or $\alpha$-direction on the wafer. It is however possible also to scan the entire surface of the wafer, while storing the scanning position of the table 20 in the y-direction and the scanning position of the laser beam spot in the x-direction when the photoelectric signal from the detector 34 exceeds the slice voltage, and to analyze thus obtained coordinate values for example with a microcomputer to determine the positions of the remaining resists P, N obtainable by the superposed exposures of the positive and negative patterns.

At the scanning of the replication area S0 by the laser beam spot, the coordinate value reading by the scattered light detection should preferably be prohibited, since the surface irregularities formed by the circuit pattern in the area S0 significantly deteriorates the S/N ratio of the detection of scattered light from the remaining resist corresponding to the foreign particle.

However such prohibition of reading is unnecessary if the apparatus is so constructed that the wafer is positioned with a high precision and the raster scanning position of the laser beam spot can be read precisely with a required resolving power.

In such case it is also possible to detect the remaining resists $P_0$ in the area S0 independently from the surface irregularities of the circuit pattern. It is therefore rendered possible to automatically identify the presence of foreign particles on the reticle R2 by determining the coordinate values $(x_P, y_P)$, $(x_N, y_N)$ of the remaining resists $P_1$–$P_5$, $N_1$–$N_5$ in the areas S1–S5 and identifying whether said coordinate values are included in the coordinate values obtained in the area S0.

In the foregoing embodiments, the marks AX, AY, A$\theta$ are formed on the wafer through the use of the mark reticle R1, and the reticles R2, R3 are generally provided also with corresponding alignment marks. Therefore the resist at the marks on the wafer may be exposed again at the exposure of the negative or positive pattern to destruct said marks. Such destruction of the marks on the wafer can however be prevented if the exposure apparatus is provided with a shutter for shielding the marks alone at the exposure through the reticle R2 or R3.

Figure 14A:
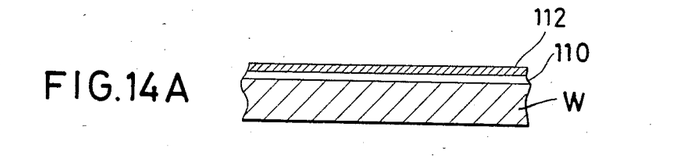
FIGS. 14A to 14D are schematic views showing replicating steps in another embodiment of the present invention.

In the aforementioned method, shown in FIGS. 5A to 5E, the alignment marks A are formed by the photoresist on the wafer through the use of the mark reticle. Consequently, if the photoresist is removed from the wafer after the inspection method, the marks A have to prepared again on said wafer when it is used in a next inspection. It is therefore convenient to prepare the marks in the following manner. At first, as shown in FIG. 14A, the wafer W is covered with a layer 110 of a material for producing semiconductor devices, such as silicon, silicon nitride, molybdenum, tungsten, PSG or polyimide, and a resist layer 112 is formed thereon.

Figure 14B:
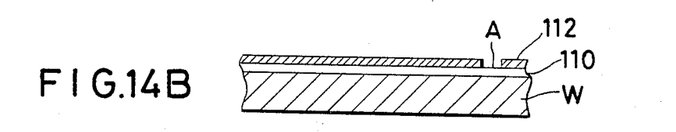
Figure 14C:
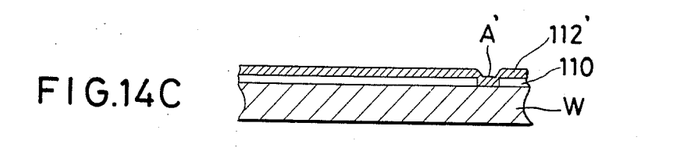

Then said wafer is exposed to the mark alone and is developed, whereby the resist layer 112 is partially removed as shown in FIG. 14B to form the mark A. Then said wafer is subjected to etching whereby the layer 110 is partially removed as shown in FIG. 14C to obtain a mark A'. Subsequently a resist layer 112' is formed thereon again.

Figure 14D:
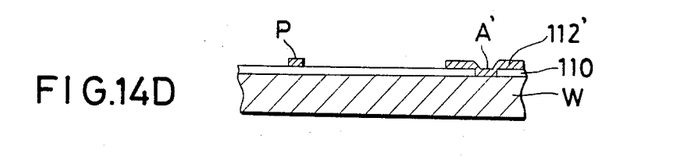

The wafer processed as shown in FIG. 14C is subsequently subjected to superposed exposure of the positive and negative patterns as in the foregoing embodiments and is developed, whereby an unexposed area, corresponding to the foreign particle, subsists as the remaining resist P on the layer 110 as shown in FIG. 14D.

The wafer W in this state can be used for inspection by scanning with the laser beam spot. In this method the marks are prepared in advance in the layer 110 on the wafer, so that the wafer can be stored without the resist 112' after the inspection and can be immediately used in a next inspection from a step shown in FIG. 14C.

Also it is possible to subject, after the remaining resist P is obtained as shown in FIG. 14D, the wafer to etching thereby removing the layer 100 except an area of the remaining resist P (resist layer 112') and forming surface irregularities by the layer 110 on the wafer and to scan the surface of the wafer with a laser beam spot.

The use of a positive photoresist is preferable since the wafer surface inspection by the laser beam scattering generally provides a higher sensitivity in a surface depression than in a surface projection, but a negative photoresist is naturally applicable also in the inspecting method of the present invention. In this case the foreign particle appears as a depression in the resist.

Now there will be explained a mask inspecting method according to a second embodiment of the present invention.

Figure 15:
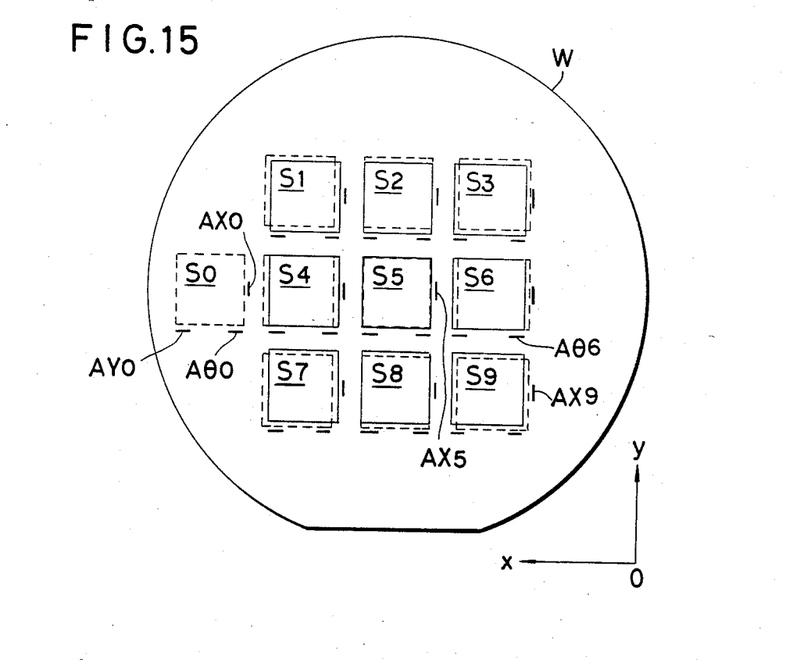
FIG. 15 is a plan view showing the positional relationship of positive and negative patterns replicated onto a wafer according to a second embodiment of the present invention.

FIG. 15 shows nine replication areas S1-S9 formed on the wafer W by replicating a negative pattern. The negative pattern areas S1-S9 arranged in matrix structure are schematically shown in solid lines though said areas are in fact invisible latent images in this state. If the marks $AY_0$, $AX_5$ and $A_{\theta 6}$ are used for the alignment between the inverted reticle R3 and the wafer, same marks will be used in the alignment between the reticle R2 and the wafer even when the exposure of the positive pattern of the reticle R2 is conducted on another exposure apparatus.

Then there is repeated a step, for each of the nine areas S1-S9, of stepwise moving the stage 5 in such a manner that the projected image of the positive pattern overlaps with the latent negative images of said areas S1-S9 and illuminating the area PA2 of the reticle R2. Each of the exposures in the above-mentioned procedure is conducted in such a manner that the projected image of the positive pattern is intentionally displaced by a small amount from each target position of the areas S1-S9.

In FIG. 15, the exposure areas of the positive patterns slightly displaced from the areas S1-S9 are represented by broken lines. The amount of said displacement can be comparable to the amount of distortion in projection or error in magnification of the projecting lens 1, or of mechanical drift, and is selected as ±0.2 μm in the present embodiment. More specifically said displacement is obtained by moving the stage 5 by 0.2 or −0.2 μm in the x- or y-direction after the detector 7 indicates that the wafer has reached the target position. The displacement of the table 5 by 0.2 μm is easily achieved if the detector 7 is composed of a laser interferometer capable of reading the position of the stage 5 with a resolving power of 0.01 μm at minimum.

The amount of said displacement ($\Delta x_n$, $\Delta y_n$) for each negative pattern replication area Sn (n=1-9) is determined as follows:

$(\Delta x_1, \Delta y_1) = (0.2, 0.2)$ $(\Delta x_2, \Delta y_2) = (0.0, 0.2)$ $(\Delta x_3, \Delta y_3) = (-0.2, 0.2)$ $(\Delta x_4, \Delta y_4) = (0.2, 0.0)$ $(\Delta x_5, \Delta y_5) = (0.0, 0.0)$ $(\Delta x_6, \Delta y_6) = (-0.2, 0.0)$ $(\Delta x_7, \Delta y_7) = (0.2, -0.2)$ $(\Delta x_8, \Delta y_8) = (0.0, -0.2)$ $(\Delta x_9, \Delta y_9) = (-0.2, -0.2)$ The figures mentioned above are represented in μm.

A positive figure indicates that the projected image of the positive pattern is slightly displaced in the positive x- or y-direction of the xy-coordinate system on the wafer W with respect to the replication area of the negative pattern, and vice versa.

In this manner the directions of displacements are all different in the nine areas S1-S9. There is no displacement in the central area S5, but in the surrounding eight areas S1-F4 and S6-S9 the projected images of the positive pattern are displaced toward the outside by 0.2 μm.

As explained in the foregoing, the projected images of the positive pattern are superposed on the latent images of the negative pattern respectively formed in the areas S1-S9 in such a manner that said projected images are slightly displaced in the x- and/or y-direction from said latent images.

Also in this case the reticle R2 is shielded so as to prevent the exposure of the marks AX, AY, Aθ. The exposure is conducted in the same manner as in the first embodiment shown in FIG. 5D. Also as in the first embodiment there is formed an area S0 which is not exposed to the negative pattern but alone to the positive pattern of the reticle R2. Subsequently the wafer W is removed from the exposure apparatus and is subjected to the development of the positive resist layer 10. Each replication area on the wafer contains not only the remaining resists resulting from the presence of foreign particles but also the remaining resists resulting from incomplete jointing of the edges of the negative and positive patterns caused by the aforementioned displacement of ±0.2 μm in each area.

Figure 16:
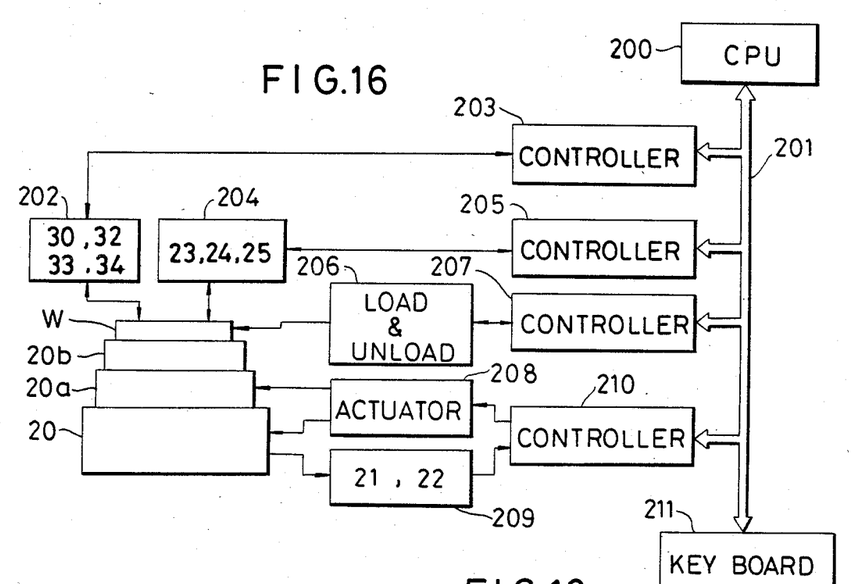
FIG. 16 is a block diagram showing another embodiment of the control system in the apparatus shown in FIG. 10.

Then effected is an inspection step for identifying the exposure status or the remaining resists on the wafer, by means of the apparatus shown in FIG. 10 and a control apparatus shown in FIG. 16.

In FIG. 16, a central processing unit (CPU) 200 composed for example of a microprocessor controls the entire apparatus through an interface bus 201. A remaining resist detecting unit 202, comprising the laser unit 30, polygonal mirror 32, photosensor 33 and photoelectric detector 34 shown in FIG. 10, is controlled by the CPU 200 through a control unit 203. Also the CPU 200 performs control, such as focusing, for a microscope unit 204 including the alignment microscopes 23, 24 and observing microscope 25 through a control unit 205.

On the other hand, the table 20 is provided with a wafer holder consisting of a rotary table 20a for rotating the wafer W and a vacuum chuck 20b. The wafer is transported by a load-unload mechanism 206 which is activated by the CPU 200 through a control unit 207. The movement of the table 20 in the x- and y-directions and the rotation of the table 20a are conducted by an actuator 208, which is activated by the CPU 200 through a control unit 210 receiving positional information from a position detecting unit 209 containing position detectors 21, 22. An operation panel 211 including a keyboard is provided for input and output of various instructions and information.

A wafer after development, as shown in FIG. 15, is placed on the apparatus shown in FIG. 10 and is scanned with the laser beam spot in the same manner as in the foregoing embodiment to obtain photoelectric signals as shown in FIG. 12C. The coordinate values corresponding to the pulses are in succession stored by the CPU 200, through $\alpha$- and $\beta$-counters of the position detectors 21, 22 or counters for measuring the scanning position of the laser beam spot. This operation is conducted for all the areas S1–S9 on the wafer.

Then, the positions of all the remaining resists in the areas S1–S9 are stored in a memory of the CPU 200 after conversion into coordinate values of each area, and the number of the remaining resists in each area is counted and stored.

Then, from said areas S1–S9 selected is an area, for example S4, containing a least number of the remaining resists. This means that the alignment of the positive and negative patterns has been achieved best in said area S4.

Thus, the examination of the remaining resists in said area S4 allows to identify the foreign particles present in the transparent area of the reticle R2. However a comparison is also made with the pattern of the remaining resists in the area S0, since the examination of the area S4 alone will also provide the defects in the reticle R3.

The foreign particles on the reticle R2 can be identified by confirming whether the area S0 contains the remaining resists ($P_0$) in positions and shapes corresponding to those of the remaining resists ($P_4$, $N_4$) in the area S4.

More specifically this is achieved by reading the positions of the remaining resists $P_4$ in the area S4 from the CPU 200, moving the table 20 so as to bring the optical axis or center of observation of the microscope 25 to the corresponding positions in the area S0, and confirming the presence of the remaining resists $P_0$ similar to the resists $P_4$.

The above-described inspection can be conducted automatically utilizing the ability of the remaining resist detecting unit 202, if the apparatus is so designed to align the wafer precisely and to read the raster scanning position of the laser beam spot with a necessary resolving power. In such case, since the scattered light generated by the remaining resists $P_0$ in the area S0 can be distinguished from that generated by the surface irregularities of the circuit pattern in the resist, it is possible to automatically detect the foreign particles on the reticle R2 by determining the coordinate values ($x_P$, $y_P$), ($x_N$, $y_N$) of the remaining resists $P_4$, $N_4$ in the area S4 and then examining whether said coordinate values are included in those of the area S0.

As explained in the foregoing, the present embodiment is featured by a fact that the positive and negative patterns are replicated in superposition onto the positive resist layer 10 with mutual slight displacements in varied directions, and the inspection is made on the resist patterns obtained after the image development. It is therefore rendered possible to always utilize an area of a high aligning precision regardless of a possible drift error of the exposure apparatus or of possible difference in alignment between two exposure apparatus, and to detect the defects in the reticle R2 in very accurate and efficient manner.

Figures 17, 18, 19:
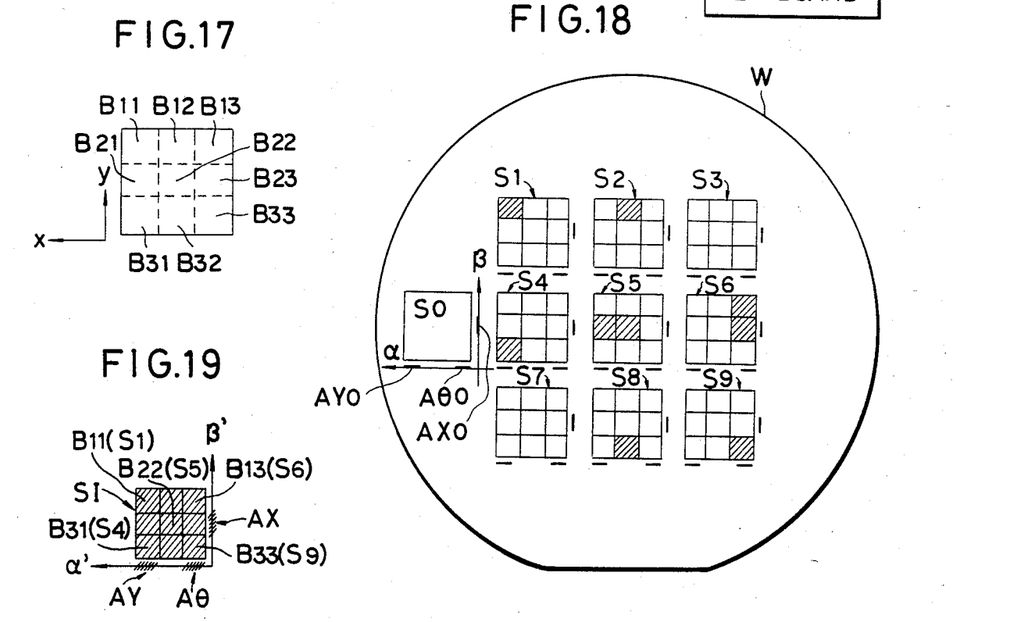
FIG. 17 is a plan view showing partial areas in a replicated area.
FIG. 18 is a plan view showing partial area selected in different replicated areas.
FIG. 19 is a plan view showing an imaginary replicated area.

Now reference is made to FIGS. 17, 18 and 19 for explaining another embodiment of the wafer inspecting method, which is same as the second embodiment up to the development step and is different only in the inspecting step.

At first the wafer W after development is placed on the wafer inspecting apparatus shown in FIG. 10 and is scanned with the laser beam spot to identify the remaining resists in each of the areas S1–S9.

Then each area is imaginarily divided by the CPU 200 into nine partial areas $B_{11}$, $B_{12}$, $B_{13}$, $B_{21}$, $B_{22}$, $B_{23}$, $B_{31}$, $B_{32}$ and $B_{33}$ arranged in a $3\times3$ matrix as shown in FIG. 17, and the number of the remaining resists in each partial area is detected. This procedure is repeated for nine areas S1–S9 as shown in FIG. 18.

Then a comparison is made on the numbers of the remaining resists among mutually corresponding partial areas of different areas.

More specifically, a comparison is made among $P_{11}(S1)$ (indicating the partial area $B_{11}$ in the area S1), $B_{11}(S2)$, $B_{11}(S3)$, $B_{11}(S4)$, $B_{11}(S5)$, $B_{11}(S6)$, $B_{11}(S7)$, $B_{11}(S8)$ and $B_{11}(S9)$ to determine a partial area containing a least number of the remaining resists, for example the partial area $B_{11}(S1)$ as indicated by a hatched area in FIG. 18. Comparisons are made similarly on other partial areas in the areas S1–S9 to select those containing least numbers of the remaining resists. FIG. 18 shows, as represented by hatched areas, an example in which partial areas $B_{11}(S1)$, $B_{12}(S2)$, $B_{13}(S6)$, $B_{21}(S5)$, $B_{22}(S5)$, $B_{23}(S6)$, $B_{31}(S4)$, $B_{32}(S8)$ and $B_{33}(S9)$. The partial areas thus selected represent where the positive and negative patterns have been best aligned.

Then the nine partial areas thus selected are combined to form an imaginary replication area SI as shown in FIG. 19 for detecting the presence and positions of the remaining resists. Said imaginary replication area SI can be considered as if the negative and positive patterns are precisely superposed without error, even when the replications of the reticles R2 and R3 are effected in different exposure apparatus in which the projecting lenses 1 are mutually different slightly in image distortion or in image magnification.

Thus, as in the second embodiment, there is defined a coordinate system $\alpha'\beta'$ in the imaginary replication area SI, and the positions of the remaining resists in said area SI are compared with those of the remaining resists in the area S0 to identify the foreign particles present on the reticle R2.

The above-described third emboidment enables extremely exact inspection of the reticle R2, even when the positive and negative patterns are replicated with different exposure apparatus, through the use of an imaginary replication area SI in which the negative and positive patterns are superposed in ideal condition over the entire area regardless of slight differences in image distortion or image magnification between the different exposure apparatus.

Besides the foregoing embodiment provides a possibility of inspection without the use of alignment marks on the wafer. For example, in case the negative and positive patterns are replicated within a short time on the same exposure apparatus, the wafer need not be removed from the exposure apparatus after the replication of the negative pattern. Consequently a considerably exact inspection can be expected even when the successive replications are made relying on the positioning precision of the reticle R2 and the stepping precision of the stage 5.

Also there can be considered various vairations in the amounts and directions of the mutual displacements between the positive and negative patterns.

For example there may be employed two wafers to form nine replication areas with displacements of ±0.2 μm on a wafer while to form other nine replication areas with displacements of ±0.1 or ±0.3 μm on the other wafer, and best aligned replication area or partial areas are selected from such 18 replication areas. Also in the foregoing embodiment a wafer includes nine replications respectively representing positional displacements in ±x-direction, ±y-direction, ±45°-direction and ±135°-direction as well as no positional displacement, but it is also possible to replicate, onto a latent image in the resist layer of the wafer, the image of a reticle after it is rotated by a small amount about the optical axis 1 of the projecting lens 1.

On the other hand the non-superposed replication area S0 need not necessarily be on the same wafer as other replications areas, but may be formed on a separate wafer. Also said area S0 may be exposed only to the negative pattern of the retice R3.

The present embodiment is particularly effective for use in an X-ray exposure apparatus enabling lithography in the sub-micron range for example with soft X-ray.

Generally in the X-ray exposure apparatus, the wafer is separated by a small distance from the mask and is exposed to the pattern of the mask by X-ray from a point source, so that the image magnification of replication fluctuates if said distance is different between the positive and negative pattern exposures. Consequently the method of the second or third embodiment is extremely effective for the inspection of mask defects in the X-ray lithography which often suffers from fluctuation in the image magnification.

In the foregoing embodiments the remaining resists are scanned with the laser beam spot to detect the scattered light from said remaining resists, but it is also possible to etch the wafer to form projections corresponding to the remaining resists and to scan said projections with the laser beam spot to detect the light scattered by the edges of said projections.

Furthermore it is possible to illuminate the wager surface in a dark field and to effect electric inspection on the image signals obtained for example from a television camera which observes the surface irregularities through a microscope.

I claim:

1. A method of inspecting a determined pattern composed of an opaque area and a transparent area on a photomask provided with alignment reference marks, comprising the steps of:
   (a) forming an inverted mask provided with an inverted pattern in which the transparent area and the opaque area are inverted with respect to said determined pattern and reference marks corresponding to the reference marks of said photomask;
   (b) forming reference marks on a substrate coated with a photosensitive material, corresponding to the reference marks of said photomask;
   (c) aligning either one of said photomask and said inverted mask by means of the reference marks of said either one mask and the reference marks of said substrate and subjecting the photosensitive material of said substrate to a first exposure through said either one mask;
   (d) aligning the other of said photomask and said inverted mask by means of the reference marks of said other mask and the reference marks of said substrate and subjecting the photosensitive material of said substrate to a second exposure through said other mask;
   (e) developing the photosensitive material of said substrate subjected to said first and second exposures; and
   (f) inspecting said substrate after development.

2. An inspecting method according to claim 1, wherein said substrate inspecting step comprises a step of scanning the surface of said substrate by means of an energy beam, and a step of detecting energy scattered by the surface of said substrate to detect defects contained in said determined pattern 3. An inspecting method according to claim 1, wherein said first exposure step is so conducted to expose plural areas on said substrate through said either one photomask, and said second exposure step is so conducted to expose said plural areas through said other mask.

4. An inspecting method according to claim 3, wherein said substrate inspecting step comprises a step of comparing patterns of said plural areas formed after said development.

5. A method for inspecting a determined pattern composed of a transparent area and an opaque area on a photomask, comprising the steps of:
   (a) replicating said determined pattern to form a first replica mask having a first negative pattern in which the transparent area and the opaque area are inverted with respect to said determined pattern;
   (b) forming a second negative pattern in which the transparent area and the opaque area are inverted with respect to said determined pattern;
   (c) replicating said second negative pattern to form a second replica mask having a positive pattern in which the transparent area and the opaque area are again inverted with respect to said second negative pattern;
   (d) projecting said first negative pattern and said positive pattern respectively onto the photosensitive material in superposed manner;
   (e) developing said photosensitive material; and
   (f) inspecting said developed photosensitive material.

6. A method for inspecting a determined pattern composed of a transparent area and an opaque area on a photomask, comprising the steps of:
   (a) forming an inverted mask having a first negative pattern in which the transparent area and the opaque area with respect to said determined pattern;
   (b) replicating said determined pattern of said photomask to form a first replica mask having a second negative pattern in which the transparent area and the opaque area are inverted with respect to said determined pattern;
(c) replicating said first negative pattern of said inverted mask to form a second replica mask having a positive pattern in which the transparent area and the opaque area are again inverted with respect to said first negative pattern;
(d) projecting said determined pattern of said photomask and said first negative pattern of said inverted mask respectively onto a first photosensitive material in superposed manner;
(e) projecting said second negative pattern of said first replica mask and said positive pattern of said second replica mask respectively onto a second photosensitive material in superposed manner;
(f) developing said first and second photosensitive materials; and
(g) inspecting said developed first and second photosensitive materials.

7. A method for inspecting a determined pattern composed of a transparent area and an opaque area on a photomask, comprising the steps of:
(a) forming an inverted mask having a negative pattern in which the transparent area and the opaque area are inverted with respect to said determined pattern;
(b) projecting said determined pattern and said negative pattern onto a first area in a photosensitive material;
(c) projecting either one of said determined pattern and said negative pattern onto a second area in said photosensitive material;
(d) developing said photosensitive material; and
(e) comparing said first and second areas on said developed photosensitive material.

8. A method for inspecting a determined pattern composed of a transparent area and an opaque area on a photomask, comprising the steps of:
(a) forming an inverted mask having a negative pattern in which the transparent area and the opaque area are inverted with respect to said determined pattern;
(b) projecting said determined pattern and said negative pattern in superposed manner and plural times on different photosensitive materials to form plural latent images;
(c) developing latent images on said photosensitive materials; and
(d) comparing said developed plural photosensitive materials.

9. A method for inspecting a determined pattern composed of a transparent area and an opaque area on a photomask, comprising the steps of:
(a) forming an inverted mask having a negative pattern in which the transparent area and the opaque area are inverted with respect to said determined pattern;
(b) first replication for replicating the pattern of either one of said photomask and said inverted mask onto plural replication areas of a photosensitive material;
(c) second replication for replicating the pattern of the other of said photomask and said inverted mask onto each of said plural replication areas, respectively with displacements of a determined amount in different directions in superposed manner on the latent images of the pattern of said either one mask;
(d) developing said photosensitive material after said first and second replications; and
(e) inspecting the exposure status of each of said developed replication areas.

10. A method for inspecting a determined pattern composed of a transparent area and an opaque area on a photomask, comprising the steps of:
(a) forming an inverted mask having a negative pattern in which the transparent area and the opaque area are inverted with respect to said determined pattern;
(b) replication for exposing a photosensitive material coated on a substrate to the pattern of said photomask and the pattern of said inverted mask in superposed manner;
(c) processing for developing said photosensitive material to form depressions and projections on the surface of said substrate corresponding to the defects present on said photomask; and
(d) scanning the surface of said substrate with an energy beam to detect the energy scattered from said surface depressions and projections.

* * * * *